United States Patent [19]

Broun, Jr.

[11] 4,010,186
[45] Mar. 1, 1977

[54] REMOVAL OF LEAD FROM AQUEOUS SOLUTION USING METALLIC MAGNESIUM

[75] Inventor: Thorowgood T. Broun, Jr., Beaumont, Tex.

[73] Assignee: PPG Industries, Inc., Pittsburgh, Pa.

[22] Filed: Apr. 5, 1971

[21] Appl. No.: 131,548

[52] U.S. Cl. .................. 260/437 R; 210/42 R; 210/59
[51] Int. Cl.² ........................................ C07F 7/24
[58] Field of Search .......... 210/42, 59; 260/437 R; 75/109, 120

[56] References Cited

UNITED STATES PATENTS

| | | | |
|---|---|---|---|
| 1,480,110 | 1/1924 | Platten | 75/109 |
| 2,666,684 | 1/1954 | Denyes | 210/42 X |
| 3,117,000 | 1/1964 | Schlain et al. | 75/109 |
| 3,308,061 | 3/1967 | Collier | 75/109 |
| 3,697,567 | 10/1972 | Taylor | 260/437 R |

*Primary Examiner*—Helen M. S. Sneed
*Attorney, Agent, or Firm*—Irwin M. Stein; John E. Curley

[57] ABSTRACT

A process is described for reducing the lead content of aqueous solution containing lead impurities in which the solution is contacted with metallic magnesium. Lead compounds are converted to water insoluble forms which are separated by recourse to physical processing such as steam distillation, filtration, settling, centrifugation, decantation and the like. In general, the process is conducted at pH of 7 to 11, preferably 8 to 9.5. Reaction temperature can be ambient temperature (25° C.) or higher. In one embodiment the reaction is conducted in a steam distillation zone. The magnesium is added at a rate to provide at least 0.5 mole of magnesium per mole of lead, preferably 0.75 mole to 1.5 moles or more of magnesium per mole of lead.

12 Claims, No Drawings

REMOVAL OF LEAD FROM AQUEOUS SOLUTION USING METALLIC MAGNESIUM

BACKGROUND OF THE INVENTION

In the manufacture of alkyl lead compounds many aqueous process streams are produced which contain dissolved organic and inorganic lead constituents. These streams represent a potential source of pollution since they possess a high lead content and for this reason must be treated to remove lead therefrom prior to disposal. When the lead present is organic in nature, and in most instances the major portion of the lead is in this state, it is difficult and often impossible to precipitate from aqueous solution.

Typically, these lead contaminated streams are formed by dropping an alkyl lead charge from the reactor in which tetraalkylleads are produced into water for recovery of the alkyl lead content thereof by subsequent steam distillation. Aqueous streams resulting from these operations normally contain both organic and inorganic lead. In conducting a redistribution reaction such as described in U.S. Pat. No. 3,151,141, it is typical to wash the product with an aqueous alkali metal hydroxide to remove the catalyst from the organic lead products produced in the reaction. This wash water normally contains very high concentrations of lead both as inorganic and organic species. Solutions of this type have organic lead in concentrations of 2 to 10 percent by weight frequently. Disposal of an aqueous stream such as this requires the removal of the contained lead therefrom and this has become a very difficult and bothersome problem since the majority of the dissolved lead present is organic in nature.

THE PRESENT INVENTION

In accordance with one embodiment of the present invention a method is provided which results in the rapid and efficient removal of dissolved organic lead from aqueous streams containing this contaminant. The method is particularly useful in removing dissolved organic lead from aqueous streams containing high concentrations of lead therein, for example, 5,000 to 100,000 parts per million or more. A stream of this type is typically produced by washing catalyst from redistribution reaction systems for redistributing alkyl radicals with alkali metal hydroxide solutions. The present invention also contemplates removal of both dissolved organic lead and dissolved inorganic lead.

The removal of dissolved organic lead from aqueous solution in accordance with this invention is accomplished by contacting the aqueous solution containing the contaminating quantities of dissolved organic lead with metallic magnesium in a concentration of at least 0.50 mole of magnesium per mole of lead present. This contact of the contaminated aqueous solution with metallic magnesium takes place for a period of time sufficient for the magnesium to convert the dissolved organic lead to solids and liquids both insoluble in the original aqueous medium. The solid lead compounds are removed by settling or filtration and the liquid insoluble lead compounds by settling and decantation or by steam distillation. Removal of the insoluble lead compounds provides an aqueous solution having substantially no dissolved organic lead therein (i.e. less than 500 parts per million).

The metallic magnesium employed in the instant invention may take any convenient form. Thus utilization of chips, turnings, granules, powders and the like is contemplated. It is preferred to utilize metallic magnesium in as small a particulate form as possible to increase the reaction rate. The use of fine granules or powdered metal is particularly useful for aqueous streams containing low concentrations of dissolved lead (i.e. 1000 parts per million or less).

In conducting the reaction between the metallic magnesium and the dissolved organic lead, the temperatures used may be varied considerably. The reaction can be conducted by mixing the magnesium with the contaminated solutions at ambient temperatures (25° C.). In general temperatures ranging between 10° C. to 110° C. are used. In one embodiment of the invention, the reaction is conducted in a steam distillation zone operating at between 100° C. to 106° C.

In general the reaction is conducted for periods of time ranging between 1 to 48 hours or more. The reaction proceeds slower at lower temperatures (10° C. to 80° C.) than it does at higher temperature (above 80° C.) up to boiling point of the solutions being treated. A steam distillation system is typically operated using this invention for a period of about two hours. Using ambient temperature the typical reaction is completed in from 10 to 48 hours. At temperature above 80° C. the reaction times are typically between 1 to 8 hours.

The invention is particularly useful in treating solutions containing high lead concentrations as dissolved organic and inorganic lead, for example 10,000 parts per million or more, generally 20,000 to 100,000 parts per million. It has been practiced for example quite successfully on solutions containing as much as 7 percent by weight lead. These solutions are reduced in lead content using the magnesium treatment described, to less than 450 parts per million in a typical run. With concentrations of lead on the order of 1000 parts per million to about 500 parts per million, treatment in accordance with this invention will reduce the lead content to 200 PPM or less, typically 20 to 100 PPM. By utilizing excess magnesium (more than 1 mole per mole of lead present dissolved) in fine particulate form, typically 1/8 inch diameter or less, and elevated temperature (80° C. to 110° C.) the instant process can be employed to treat solutions containing small quantities of dissolved organic lead (i.e. 200 parts per million or less). In these instances the dissolved organic lead can be reduced to less than 20 parts per million.

The magnesium metal is used in the reaction systems of the instant invention in quantities typically ranging between 0.50 to 1.5 mole of magnesium per mole of dissolved organic lead present. Molar quantities of magnesium in excess of 1.5 may be used without detracting from the process. The limiting factor in using excess magnesium is the cost involved since satisfactory results are obtained with 1.5 moles of magnesium per mole of dissolved organic lead. Magnesium normally should not be used in quantities below 0.50 mole per mole of organic lead since adequate removal is not normally experienced.

The reaction is conducted in any suitable apparatus lending itself to the quantity of fluid treated, the temperature to be employed and other similar considerations. Thus, conventional steam still equipment may be used to conduct the process where steam distillation is used to heat the solutions during treatment. The use of reflux in a column affixed to a suitable tank in which the solutions are located and boiling is also contemplated. Where reactions are conducted at ambient temperature, the use of stirred vessels or ponds equipped with agitation means is contemplated.

In a further embodiment of the invention applied to solution containing quantities of dissolved inorganic lead in addition to dissolved organic lead, it is preferred that an adjustment of the pH of the solutions treated be made should their pH exceed 9 before and/or after the magnesium treatment. Thus, solutions containing dissolved inorganic lead at a pH of above 9.5 after treatment with magnesium may be adjusted with acid to provide a pH in the solution of 9.5 or below. Preferably the pH is adjusted to between about 8 and about 9.5. This pH adjustment precipitates dissolved inorganic lead present in the solution. The lead so precipitated is subsequently removed by filtration, centrifugation or other similar procedure. If desired, pH adjustment to a pH between about 8 to about 9.5 may be practiced prior to the magnesium treatment with the added advantage of minimizing magnesium consumption in production of hydrogen but this is not required.

In the preferred operation of the instant invention on solution containing dissolved organic and inorganic lead, the pH adjustment of the aqueous solution is practiced after the magnesium metal treatment step. This pH adjustment renders water soluble inorganic lead compounds water insoluble in accord with the steps described generally in U.S Pat. No. 3,308,061. When used in conjunction with the metallic magnesium treatment herein described aqueous streams containing both organic and inorganic soluble lead compounds may be readily purified to a low lead content.

In the adjustment of pH the presence of chloride ions introduced when utilizing HCl as the acid to adjust pH has a favorable effect on the process. In those instances where pH is adjusted prior to the addition of the magnesium, it is preferred that HCl be employed for this adjustment and in quantity sufficient to provide at least about 0.1 weight percent chloride ions in solution. Generally between 0.1 to 3 weight percent chloride ions in solution are provided, preferably between 0.2 to 1 percent. Thus, in the preferred form of practicing this invention a pH adjustment to the 8 to 9.5 range is made with HCl with between 0.2 to 1 percent chloride ion being supplied to insure maximum benefits from the metallic magnesium treatment.

Generally the water soluble organic lead compounds that are found in the various wash waters of a tetraalkyllead plant are those having the typical formula $R_{4-n}PbX_n$ where R stands for methyl and ethyl, X for chloride or hydroxide and n equals 1 or 2. Typical of the contaminating soluble organic lead compounds found in these solutions are trialkyllead chlorides, trialkyllead hydroxides, dialkyllead dichlorides and dialkyllead dihydroxides.

The following examples typify the practice of the instant invention as applied to several specific aqueous solutions.

EXAMPLE I 200 grams of an aqueous solution containing 4.2 percent by weight dissolved organic lead, 0.2 percent by weight inorganic lead and 4 percent by weight NaOH was placed in a 1 liter resin, stirred reaction kettle, the cover of which was fitted with a gland and shaft to drive an agitator blade and with a reflux condenser. The solution was then treated with HCl to adjust the pH to 9.0. When the solution had attained a pH of 9.0, magnesium metal chips were added to the solution, the kettle cover and electric heater were put in place, and the mixture was heated to boiling and then maintained under total reflux for 1.5 hours. Using this method of treatment and varying the amount of magnesium used, a series of runs were made. After the refluxing was discontinued, the solutions were filtered for removal of solids, then centrifuged and decanted for removal of the water-insoluble liquid phase. The clear aqueous phase was analyzed for inorganic and organic lead species using a polarograph. The results of these runs and the atomic ratio of magnesium to lead used in each run is shown in Table 1:

Table 1

| Run No. | Atomic Ratio Mg/Pb | Total Pb Dissolved In Filtrate by Wt. Percent |
|---|---|---|
| 1 | .33 | 0.630 |
| 2 | .66 | 0.041 |
| 3 | 1.31 | 0.009 |

EXAMPLE II

Using the same reaction vessel as in Example I, 200 grams of solution containing 6 percent by weight organic lead, 0.01 percent inorganic lead and 2.3 percent NaOH were charged thereto. HCl was added to the solution to adjust the pH thereof to 9.0. The solution was then heated to boiling after first adding thereto varying amounts of magnesium metal chips. The boiling solution was maintained under total reflux for 1.5 hours, filtered and the filtrate analyzed for lead using a polarograph. The quantities of magnesium used in the runs and the results obtained are shown below in Table 2:

Table 2

| Run No. | Atomic Ratio Mg/Pb | Total Pb Dissolved In Filtrate by Wt. Percent |
|---|---|---|
| 1 | 0.5 | 0.76 |
| 2 | 1.0 | 0.021 |
| 3 | 2.0 | 0.025 |

EXAMPLE III

A solution identical to the solution of Example II was charged to the reactor described in Example I. The solution was not adjusted in pH. Magnesium chips were added to the solution in a quantity sufficient to provide an atomic ratio of magnesium to lead of 1.0. The beaker was heated to boil the contents and was maintained under total reflux for 1.5 hours. The solution was then filtered and the filtrate analyzed for its lead content by polarograph. The filtrate was found to contain 0.05 percent by weight lead.

In similar tests of solutions containing dissolved organic lead on the order of 2 to 10 percent by weight, it is found that reaction rate and lead removal are less dependent on alkali concentration than other factors. Thus, in solutions that contain alkali metal hydroxide below 2 percent by weight for example the magnesium treatment of the instant invention has been found to be especially effective in reducing lead values to below 200 parts per million. This is exemplified by the following:

EXAMPLE IV

Into a 1 liter resin reaction kettle was placed an aqueous solution of alkali metal hydroxide having alkalinity equivalent to 1.7 percent sodium hydroxide and containing 7.6 percent by weight dissolved lead. To this solution metal chips of magnesium were added in a quantity to supply 1 mole of magnesium for each mole of lead present. The solution was heated to boiling and maintained under total reflux for 1.5 hours. The liquor was then treated by addition thereto of HCl until the pH reached 9. The liquor was then filtered, centrifuged and decanted for determination of lead content by polarograph and EDTA complexometric titration. The filtrate contained 200 parts per million lead, of which less than 3 ppm was organic lead.

EXAMPLE V

In a further experiment an aqueous solution having alkalinity equivalent to 3.1 percent sodium hydroxide therein and containing 4.7 percent by weight lead was placed in a beaker. To the beaker was added 1.6 moles of magnesium metal chips per mole of lead. The solution was boiled and maintained under total reflux for 1.5 hours. The solution was then treated with HCl to adjust pH to 9. The solution was then filtered and the filtrate was analyzed for lead by polarograph. The lead content of the filtrate was found to be 100 parts per million.

EXAMPLE VI

In a further example a solution containing 2.07 percent NaOH by weight and having 6.1 percent dissolved lead therein at pH of 10.2 was charged to a 4.3 liter laboratory still pot. To this pot was added 5.9 grams of magnesium turnings (1 mole magnesium per mole of lead). The mixture was steam distilled at 102° C. for 1.5 hours. The solution pH was adjusted to 9.0, then filtered and the filtrate was analyzed for total lead and found to contain 0.051 percent by weight lead.

To demonstrate the effectiveness of the presence of chloride ion in enhancing results, a series of runs were made following the procedures of Example I. The solution treated was an alkaline caustic solution having an alkalinity equivalent to 0.9 percent sodium hydroxide to which magnesium chips were added to supply 1 mole of magnesium per mole of lead present. The chloride ions were added as HCl and NaCl.

The solutions treated had a total dissolved lead content of 6.8 percent by weight. One (1) percent by weight of the lead was triethyllead. The pH of the solutions before addition of metal and chloride was 9.2. The results are shown below in Table 3:

TABLE 3

| Run | Chloride Added Form | Chloride Added Molality | Dissolved Lead Wt. % Total Pb | Dissolved Lead Wt. % Triethyl Lead | pH |
|---|---|---|---|---|---|
| 1 | nil | nil | 0.24 | 0.046 | 9.2 |
| 2 | HCl | .20 | 0.028 | 0.001 | 9.7 |
| 3 | NaCl | .33 | *0.009 | 0.001 | 12.2 |
| 4 | NaCl | .17 | *0.016 | 0.001 | 11.8 |
| 5 | NaCl | .08 | 0.016 | 0.001 | 10.2 |

*pH adjusted to 9.0 before filtration and analysis.

While the invention has been described with reference to certain specific embodiments and illustrative examples, it is not intended that the invention be so limited except insofar as appears in the accompanying claims.

I claim:

1. A method of reducing the dissolved organic lead content of aqueous solution resulting from manufacture of alkyllead compound, said aqueous solution containing contaminating quantities of dissolved organic lead and having a pH of from 7 to 11, comprising contacting said solution with at least 0.50 moles of metallic magnesium per mole of dissolved organic lead, said solution containing at least 0.1 weight percent added chloride ions, for a period of time sufficient to produce lead compounds that are insoluble in said solution, and separating insoluble lead compounds from the aqueous solution, thereby providing an aqueous solution containing substantially reduced levels of dissolved organic lead.

2. The method of claim 1 wherein from 0.50 to 1.5 moles of metallic magnesium per mole of dissolved organic lead is used.

3. The method of claim 1 wherein the temperature of the aqueous solution is from 10° C. to 110° C.

4. The method of claim 1 wherein the time period is from 1 to 48 hours.

5. The method of claim 1 wherein the chloride ion is provided by hydrochloric acid or sodium chloride.

6. The method of claim 1 wherein the pH of the aqueous solution contacted with metallic magnesium is between 8 and 9.5.

7. The method of claim 1 wherein from 0.1 to 3 weight percent chloride ions are present in the solution.

8. A method of reducing the dissolved organic lead content of aqueous solution produced from washing the product of a redistribution reaction during manufacture of alkyllead compound with aqueous alkali metal hydroxide, said aqueous solution containing contaminting quantities of dissolved organic lead and having a pH of from 7 to 11, comprising contacting said solution with at least 0.50 moles of metallic magnesium per mole of dissolved organic lead, said solution containing from 0.1 to 3 weight percent added chloride ions, at from 80° C. to the boling point of the solution and for from 1 to 48 hours, to produce lead compounds that are insoluble in said solution and separating insoluble lead compounds from the aqueous solution, thereby providing an aqueous solution containing substantially reduced levels of dissolved organic lead.

9. The method of claim 8 wherein the metallic magnesium and aqueous solution are contacted in a steam distillation zone.

10. The method of claim 8 wherein from 0.50 to 1.5 moles of metallic magnesium per mole of dissolved organic lead is used and the pH of the aqueous solution contacted with metallic magnesium is between 8 and 9.5.

11. The method of claim 10 wherein the chloride ion is provided by hydrochloric acid or sodium chloride.

12. The method of claim 8 wherein the solution contains from 0.2 to 1 weight percent chloride ions.

* * * * *